(12) United States Patent
Matkovic (10) Patent No.: US 11,666,673 B2
(45) Date of Patent: Jun. 6, 2023

(54) FOOD INGREDIENT TRANSFER DEVICE (71) Applicant: Tetra Laval Holdings & Finance S.A., Pully (CH)

(72) Inventor: Marko Matkovic, Höör (SE)

(73) Assignee: Tetra Laval Holdings & Finance S.A., Pully (CH)

( * ) Notice: Subject to any disclaimer, the term of this patent is extended or adjusted under 35 U.S.C. 154(b) by 1024 days.

(21) Appl. No.: 16/470,367

(22) PCT Filed: Nov. 23, 2017

(86) PCT No.: PCT/EP2017/080141
§ 371 (c)(1),
(2) Date: Jun. 17, 2019

(87) PCT Pub. No.: WO2018/114201
PCT Pub. Date: Jun. 28, 2018

(65) Prior Publication Data
US 2020/0108161 A1   Apr. 9, 2020
US 2020/0108161 A1   Apr. 9, 2020

(30) Foreign Application Priority Data

Dec. 20, 2016   (EP) .................................... 16205269

(51) Int. Cl.
*A61L 2/07*   (2006.01)
*A23L 3/00*   (2006.01)
(Continued)

(52) U.S. Cl.
CPC ................. *A61L 2/07* (2013.01); *A23L 3/001* (2013.01); *A23L 3/22* (2013.01); *A61L 2/208* (2013.01);
(Continued)

(58) Field of Classification Search
CPC ... A23L 3/001; A23L 3/22; A61L 2/07; A61L 2/208; A61L 2/26; A61L 2202/122; A23V 2002/00
(Continued)

(56) References Cited

U.S. PATENT DOCUMENTS 4,919,658 A * 4/1990 Badia .................... A61M 5/162
604/199
5,167,816 A * 12/1992 Kruger ................ A61M 1/1662
210/257.2
(Continued)

FOREIGN PATENT DOCUMENTS

DE   10 2013 201209 A1   7/2013
EP        0918562 B1   3/2003
(Continued)

OTHER PUBLICATIONS

International Search Report for corresponding Application No. PCT/EP2017/080141, dated Jan. 3, 2018.
Extended European Search Report for corresponding Application No. 16205269.0, dated Mar. 22, 2017.

*Primary Examiner* — David G Cormier
*Assistant Examiner* — Thomas Bucci
(74) *Attorney, Agent, or Firm* — Renner, Otto, Bolsselle & Sklar, LLP (57) ABSTRACT

A food ingredient transfer device is provided. The food ingredient transfer device includes a dosing device configured to receive a food ingredient, and a first chamber that is provided with an inlet and an outlet for allowing the dosing device to pass through the first chamber. The food ingredient transfer device further includes a second chamber arranged adjacent to the first chamber for receiving the dosing device when it has passed through the first chamber, the second chamber being provided with an outlet for allowing the dosing device to pass through the second chamber and into
(Continued)

an enclosure that contains a food product to which the food ingredient shall be transferred.

13 Claims, 6 Drawing Sheets

(51) Int. Cl.
    *A61L 2/20*           (2006.01)
    *A61L 2/26*           (2006.01)
    *A23L 3/22*           (2006.01)
    *F04B 13/00*         (2006.01)

(52) U.S. Cl.
    CPC ............... *A61L 2/26* (2013.01); *F04B 13/00* (2013.01); *A23V 2002/00* (2013.01); *A61L 2202/122* (2013.01); *A61L 2202/15* (2013.01)

(58) Field of Classification Search
    USPC .......................................................... 426/281
    See application file for complete search history.

(56) References Cited

U.S. PATENT DOCUMENTS

| | | | |
|---|---|---|---|
| 6,254,269 B1 * | 7/2001 | Ernstson | B01F 25/30 |
| | | | 366/152.2 |
| 2011/0008206 A1 * | 1/2011 | Larsen | A61L 2/07 |
| | | | 422/26 |
| 2013/0237916 A1 * | 9/2013 | Hanson | A61M 5/158 |
| | | | 604/151 |
| 2015/0140183 A1 * | 5/2015 | Assing | A23L 3/001 |
| | | | 422/26 |
| 2016/0058902 A1 * | 3/2016 | Goncalves Da Costa | ............. |
| | | | B65D 77/0426 |
| | | | 137/551 |

FOREIGN PATENT DOCUMENTS

| | | | | |
|---|---|---|---|---|
| WO | WO-9320885 A1 * | 10/1993 | .......... | A61M 5/1409 |
| WO | 97/46308 A1 | 12/1997 | | |
| WO | 2016/014584 A1 | 1/2016 | | |

\* cited by examiner

FOOD INGREDIENT TRANSFER DEVICE

TECHNICAL FIELD

The invention relates to a food ingredient transfer device, and a method of transferring a food ingredient.

BACKGROUND ART

Transfer of food ingredients is commonly used within the food and beverage processing industry. In particular, such transfer may e.g. be performed when a specific food ingredient is to be added to an existing amount of base product. Examples include the addition of enzymes, colourants, flavouring agents, vitamins, salt and rennet solutions, probiotics, etc. at a relatively low amount compared to amount of the base product. Examples of base products include milk, yoghurt, cream, juice, pudding and soya.

As the resulting food product is associated with high hygienic standards, aseptic transfer of the food ingredient into the base product is normally required.

Several techniques for aseptic transfer of food ingredients have been suggested. For example, in EP0918562 an ingredient transfer device is described having a dosing needle being insertable into a flow pipe via a flexible membrane. Once the dosing needle is inserted into the flow pipe, the food ingredient may be injected into the base product flowing inside the flow pipe. Before penetrating the flexible membrane the dosing needle is flushed with sterilizing liquid.

Another example of a transfer device is taught by US2015/0140183, also relying on the principle of exposing the needle to a sterilizing agent before coming into contact with the base product.

The prior art described above successfully improves the hygienic conditions of the food ingredient transfer. However, aseptic conditions are critical and must be ensured. Therefore authorities like the Food and Drugs Administration in the United States normally require additional safety measures for reducing or even eliminating the risk of contamination during the dosing of food ingredients.

SUMMARY

It is an object of the invention to at least partly overcome one or more of the above-identified limitations of the prior art. In particular, it is an object to provide a simple yet robust solution for aseptic transfer of food ingredients which reduces or practically eliminates risks for contamination.

To solve these objects a food ingredient transfer device is provided. The food ingredient transfer device comprises a dosing device configured to receive a food ingredient, and a first chamber that is provided with an inlet and an outlet for allowing the dosing device to pass through the first chamber. The food ingredient transfer device further comprises a second chamber being arranged adjacent to the first chamber for receiving the dosing device when it has passed through the first chamber, the second chamber being provided with an outlet for allowing the dosing device to pass through the second chamber and into an enclosure that contains a food product to which the food ingredient shall be transferred.

The food ingredient transfer device is advantageous in that the risk for contamination is significantly reduces or even eliminated since each chamber may contribute to sterilizing of the dosing device.

According to a second aspect, a method for transferring a food ingredient is provided. The method comprises pushing a dosing device through a first chamber that is provided with an inlet and an outlet for allowing the dosing device to pass through the first chamber, pushing the dosing device through a second chamber that is arranged adjacent to the first chamber and provided with an outlet for allowing the dosing device to pass through the second chamber, pushing the dosing device into an enclosure that is arranged adjacent to the second chamber and contains a food product that shall receive the food ingredient, and passing the food ingredient through the dosing device, into the food product in the enclosure.

Still other objectives, features, aspects and advantages of the invention will appear from the following detailed description as well as from the drawings. Each feature described and implemented for the ingredient transfer device may be implemented for the ingredient transfer method, and vice versa.

BRIEF DESCRIPTION OF THE DRAWINGS

Embodiments of the invention will now be described, by way of example, with reference to the accompanying schematic drawings, in which.

DETAILED DESCRIPTION

Figure 1:
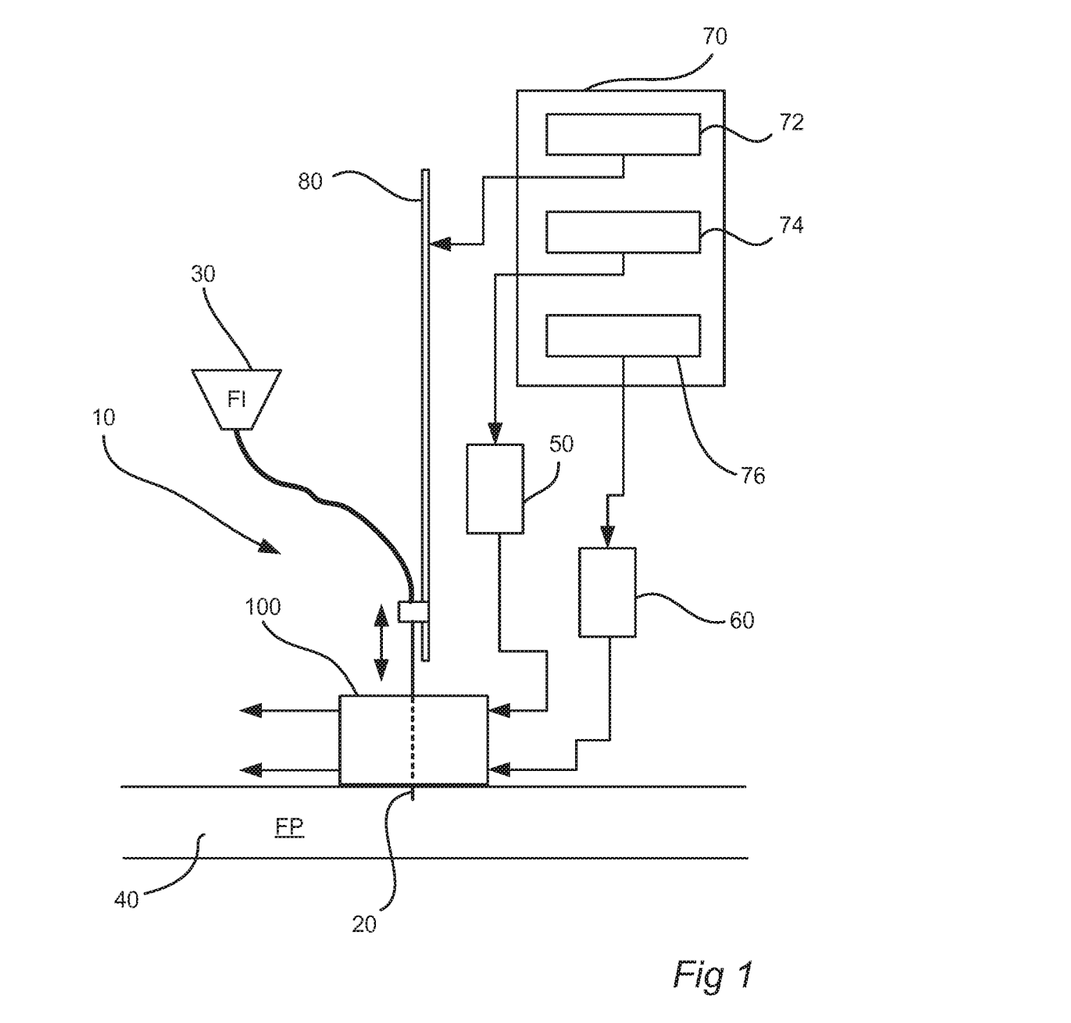
FIG. 1 is a schematic view of a food processing system comprising a food ingredient transfer device.

With reference to FIG. 1 a food processing system 10 is shown schematically. The food processing system 10 has a dosing device 20 for passing a food ingredient FI through the dosing device 20, into an amount of food product FP provided in an enclosure 40. The dosing device 20, here in the form of a dosing needle, forms part of a food ingredient transfer device 100.

The enclosure 40 is represented as a tubular conduit. As is readily understood, the enclosure 40 could also be realized as a tank or vessel, a fluid conduit, or any other structure suitable for enclosing or conveying food products within a food processing system 10.

The food ingredient transfer device 100 is arranged in close proximity to the enclosure 40 such that the dosing device 20 can be inserted into the enclosure 40 via the food ingredient transfer device 100. Any suitable, conventional technique may be used for aseptically connecting the food ingredient transfer device 100 to the enclosure 40. Hence, the food ingredient transfer device 100 forms an aseptic passageway for the dosing device 20 on its way into the enclosure 40.

The dosing device 20 is in fluid communication with a food ingredient supply 30 such that food ingredients FI may flow from the supply 30 to the enclosure 40 via the dosing device 20.

A controller 70 is provided, and included in the food processing system 10, for controlling the operation of the food ingredient transfer device 100. The controller 70 has a first unit 72 configured to control the movement of the dosing device 20, i.e. the movement towards and away from the enclosure 40. For example, the unit 72 may be in communication with a linear motor 80 or similar structure being capable of allowing for such movement of the dosing device 20. It should be appreciated that only the dosing device 20 is moveable—normally the enclosure 40, as well as further parts of the food ingredient transfer device 100, are stationary.

The controller 70 is configured to control the operation of two individual supplies 50, 60. For this, the controller 70 is provided with two additional units 74, 76. The first supply 50, being associated with the controller unit 74, is configured to supply a first fluid to the food ingredient transfer device 100. In a similar manner the second supply 60, being associated with the controller unit 76, is configured to supply a second fluid to the food ingredient transfer device 100.

As is readily understood, the units 72, 74, 76 may be provided as a single unit of the controller 70, or they may be provided as separate units or modules whereby the controller 70 represents the joint ability to control the movement of the dosing device 20, as well as the operation of the supplies 50, 60.

Now turning to FIG. 2 the food ingredient transfer device 100 will be described in further detail. Compared to the schematic illustration of the food ingredient transfer device 100 shown in FIG. 1, the embodiment shown in FIG. 2 differs in that two dosing devices 20a, 20b are present. These two dosing devices 20a, 20b may be controlled individually by means of the controller 70. The exact number of dosing devices 20a, 20b may be altered depending on the particular application.

In addition to the dosing devices 20a, 20b the food ingredient transfer device 100 comprises a housing 105 being configured to be fixedly attached to the enclosure 40, as previously described. Such attachment may thus be accomplished by, for example, means of standard equipment such as screws, bolts, etc (not shown).

The housing 105 is provided with a first chamber 110 having at least one inlet 112a, 112b for allowing the dosing devices 20a, 20b to enter the first chamber 110. In addition, the first chamber 110 is provided corresponding number of outlets 114a, 114b for allowing the dosing devices 20a, 20b to pass through the first chamber 110. Further, the housing 105 is also provided with a second chamber 120 being arranged adjacent to the first chamber 110 for receiving the dosing device 20a-b when it has passed through the first chamber 110. The second chamber 120 is provided with at least one outlet 124a, 124b for allowing the dosing device 20 to pass through the second chamber 120 and into the enclosure 40 that contains the food product FP to which the food ingredient FI shall be transferred.

Figure 2:
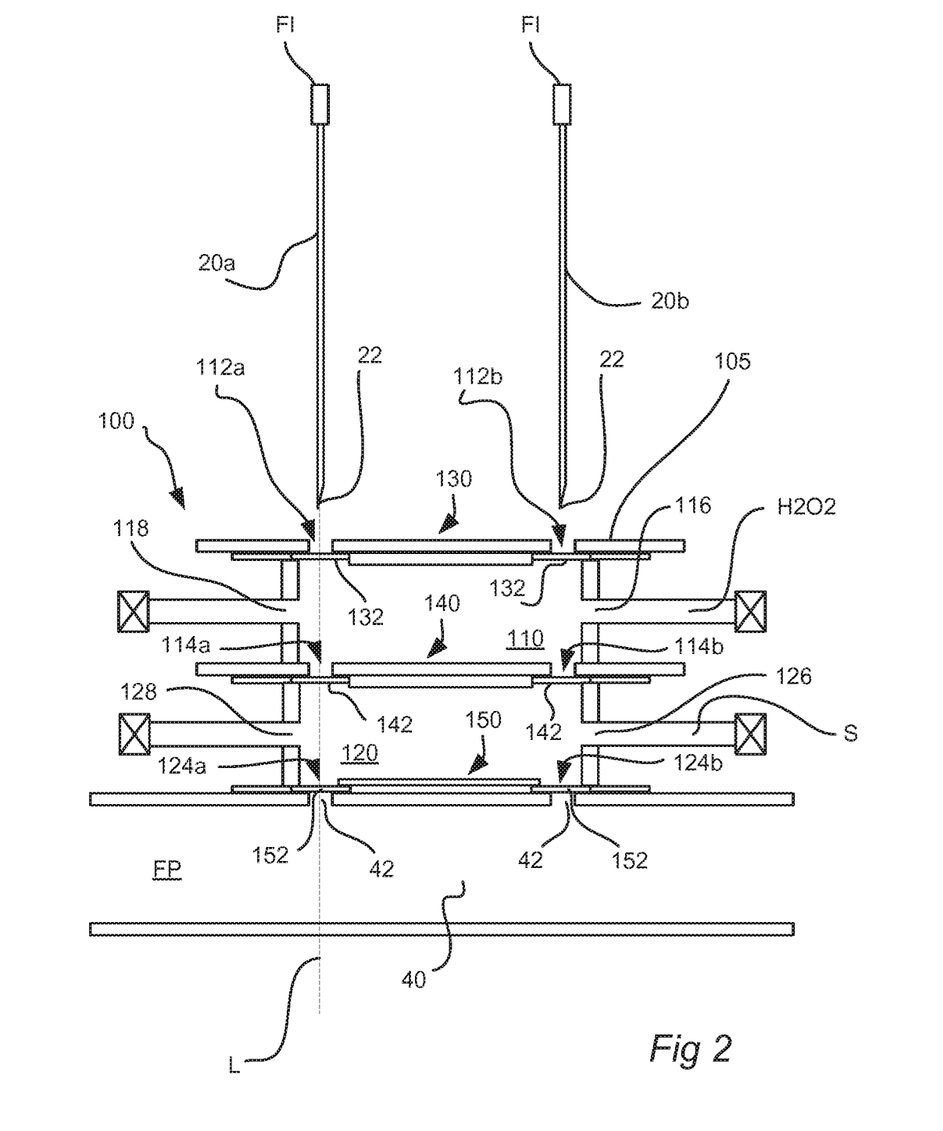
FIG. 2 is a schematic view of a food ingredient transfer device shown in a first position.

As is evident from FIG. 2, the outlets 114a, 114b of the first chamber 110 also act as inlets to the second chamber 120.

The inlets 112a, 112b form part of a sealed interface 130 between ambient conditions and the first chamber 110. The outlets 114a, 114b of the first chamber 110 form part of a sealed interface 140 between the first chamber 110 and the second chamber 120, while the outlets 124a, 124b of the second chamber 120 form a sealed interface 150 between the second chamber 120 and the enclosure 40.

In order to allow the dosing devices 20a, 20b to pass into the enclosure 40, the enclosure 40 is provided with conventional apertures 42 being aligned with the outlets 124a, 124b of the second chamber 120.

The sealed interfaces 130, 140, 140 are formed by penetrable membranes. Hence, a first penetrable membrane 132 is arranged to seal a respective inlet 112a, 112b of the first chamber 110. A second penetrable membrane 142 is arranged to seal a respective outlet 114a, 114b of the first chamber 110, and a third penetrable membrane 152 is arranged to seal a respective outlet 124a, 124b of the second chamber 120.

Considering membranes 132, 142, 152 being arranged to be penetrated by the same dosing device 20a, 20b, the first penetrable membrane 132, the second penetrable membrane 142 and the third penetrable membrane 152 are aligned in a linear direction L that extends from the first penetrable membrane 132 to the third penetrable membrane 152.

Figure 4:
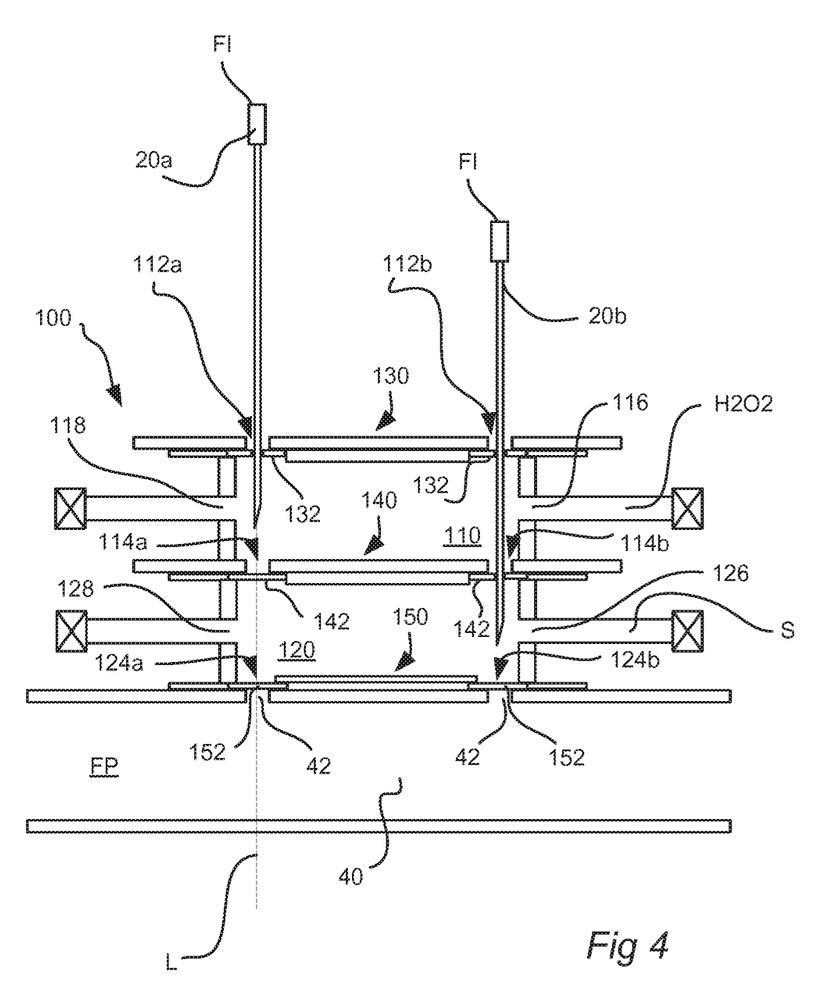
FIG. 4 is a schematic view of the food ingredient transfer device shown in a third position.
Figure 5:
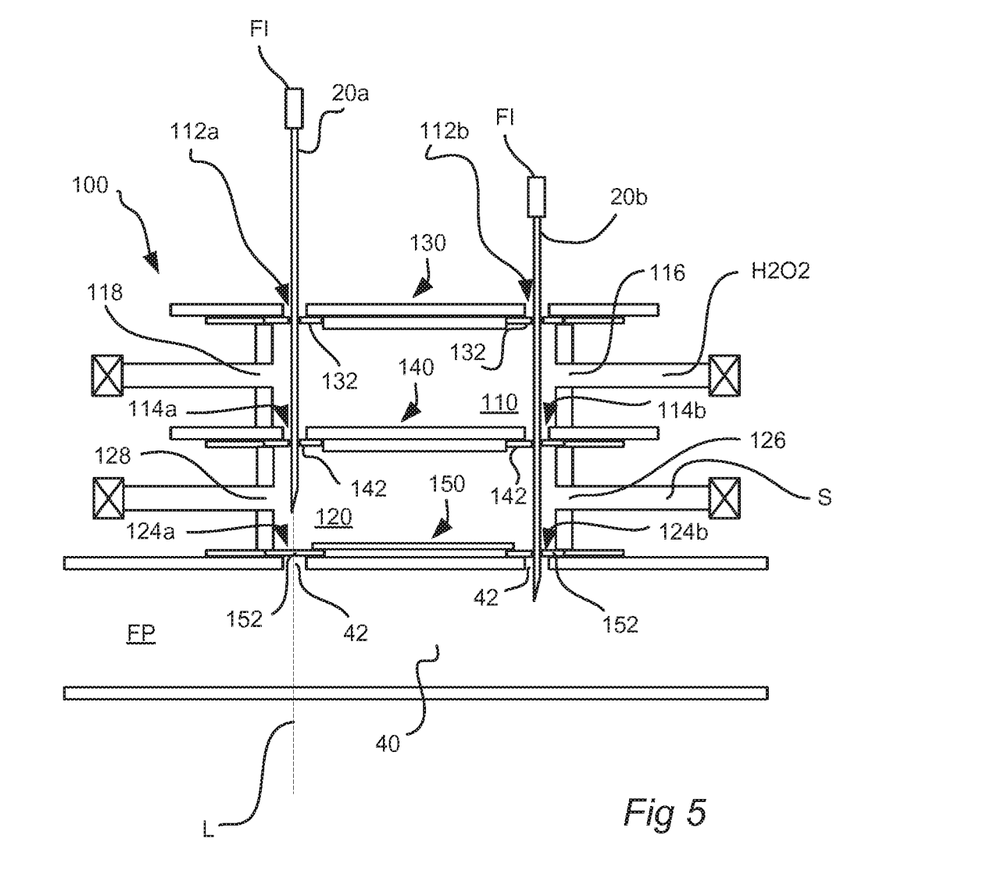
FIG. 5 is a schematic view of the food ingredient transfer device shown in a fourth position.

During operation, a dosing device 20a, 20b is moved towards the housing 105, penetrates the first membrane 132 in order to pass into the first chamber 110 (see FIG. 3), penetrates the second membrane 142 in order to pass into the second chamber 120 (see FIG. 4), and penetrates the third membrane 152 in order to pass into the enclosure 40 (see FIG. 5).

Each chamber 110, 120 is configured to contribute to the sterilization of the dosing device 20a, 20b prior to being inserted into the enclosure 40, where it contacts the food product FP.

For this, the first chamber 110 comprises an inlet port 116 and an outlet port 118 for receiving respectively expelling a first fluid, and the second chamber 120 comprises an inlet port 126 and an outlet port 128 for receiving respectively expelling a second fluid S. The first chamber 110 is thus in fluid communication with the first supply 50 (see FIG. 1) via the inlet port 116, and the second chamber 120 is in fluid communication with the second supply 60 (see FIG. 1) via the inlet port 126. Optionally, the respective outlet ports 118, 128 may be in fluid communication with return conduits in order to form closed circuits for the respective fluids.

The first fluid, flowing into the first chamber 110 via the inlet port 116, may be hydrogen peroxide $H_2O_2$. Hence, the supply 50 may provide a flow of hydrogen peroxide.

The second fluid, flowing into the second chamber 120 via the inlet port 126, may be steam S, i.e. hot vapor formed by water. Hence, the supply 60 may provide a flow of steam.

The controller 70 is not only configured to control on/off functionality of the supply of hydrogen peroxide and steam, but also controls parameters of the respective fluid like temperature, pressure, and, in the case of hydrogen peroxide, concentration.

Operation of the food ingredient transfer device 100 will now be described with reference to FIGS. 2-5. In FIG. 2, already described, the dosing devices 20a, 20b are positioned in an idle position in which they are not yet pushed into the first chamber 110. Before operation of the food ingredient transfer device 100 is initiated, the first and second chambers 110, 120 may be sterile, since the ingredient transfer device 100 may be assembled in sterile conditions.

When it is determined that dosing of a food ingredient FI is to be started, the controller 70 is programmed to initiate filling of the second chamber 120 with steam S from the second supply 60. The heat of the steam S is increasing the temperature of the first chamber 110. The steam may also provide (additional) sterilization of the second chamber 120.

Figure 3:
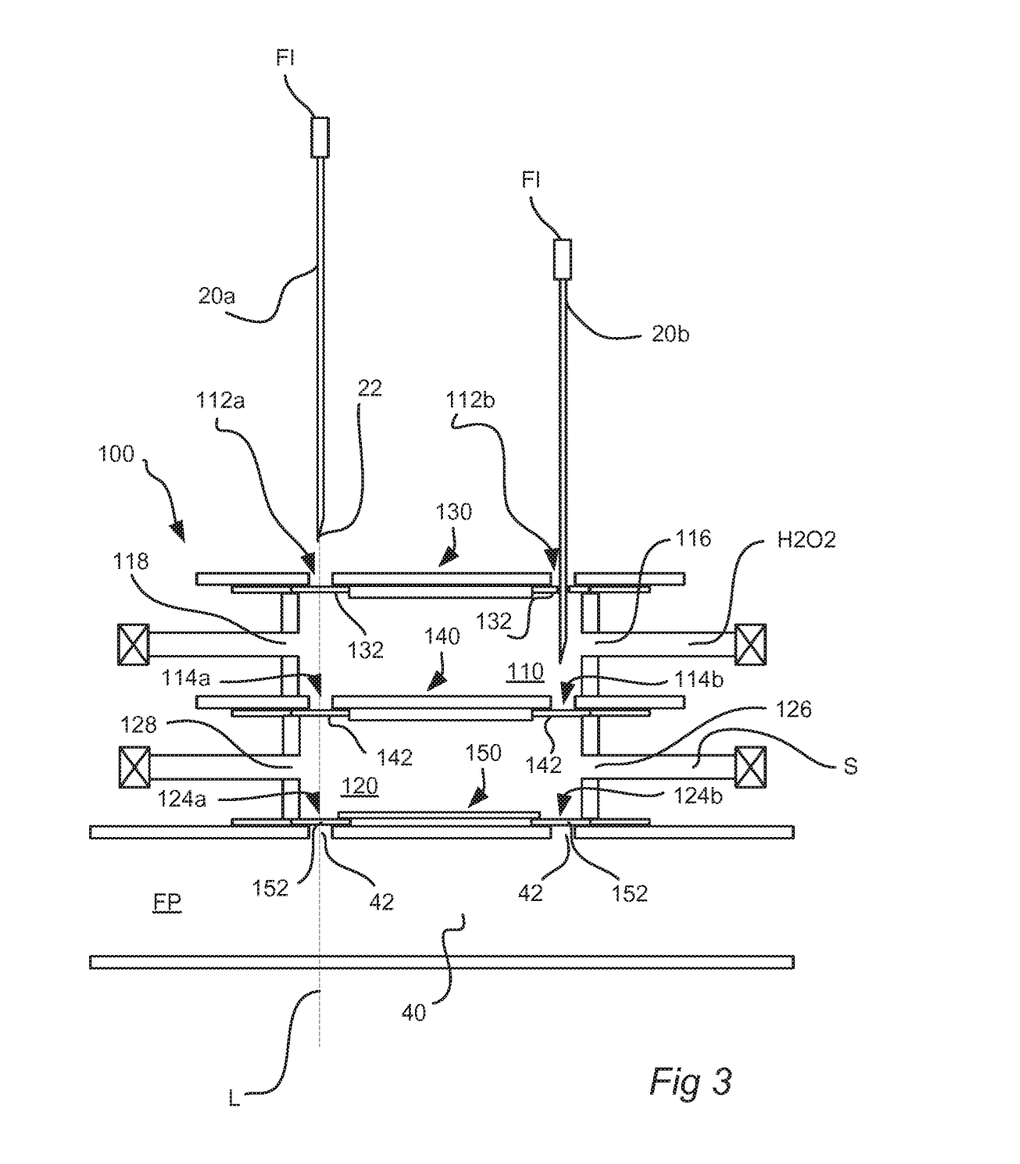
FIG. 3 is a schematic view of the food ingredient transfer device shown in a second position.

In the next step, shown in FIG. 3, the dosing device 20b is pushed downwards until a distal end 22 of the dosing device 20b penetrates the first membrane 132. When in this position, or prior to the actual penetration of the first membrane 132, the controller 70 is programmed to start providing hydrogen peroxide $H_2O_2$ to the first chamber 110. Hence, hydrogen peroxide $H_2O_2$ is fed from the first supply 50 to the first chamber 110. The concentration of hydrogen peroxide H2O2 may e.g. be 2000-3000 ppm, the differential pressure may be 100 Pa, and the temperature may be around 55° C. Preferably, the position shown in FIG. 3 may be maintained during a predetermined time of approximately 2 minutes in order to ensure full sterilization of the distal end 22 of the dosing device 20b, as well as the entire first chamber 110.

The steam in the second chamber 120 provides heat to the ingredient transfer device 100, including to the first chamber 110 and to hydrogen peroxide H2O2 inside the chamber 110, so that the hydrogen peroxide H2O2 reaches a temperature that is most efficient for obtaining proper sterilization conditions (e.g. around 55° C.). Additionally or alternatively, other heating means are used for giving the hydrogen peroxide H2O2 the desired temperature.

Before the dosing device 20b is pushed into the second chamber 120, the first chamber 110 is flushed with sterile air in order to evacuate hydrogen peroxide H2O2 from the first chamber 110.

In FIG. 4 the next position is shown, in which the dosing device 20b is moved downwards into the second chamber 120. At the same time the other dosing device 20a may be pushed into the first chamber 110, if required. However, for describing the operating principle of the food ingredient transfer device 100 the main focus will be on the movement of the dosing device indicated by reference numeral 20b.

When the dosing device 20b is pushed into the second chamber 120, the dosing device 20b may be controlled to bleed, or aerate in order to remove all air inside the dosing device 20b. When this is done, the dosing device 20b proceeds downwards into the enclosure 40 by penetrating the third membrane 152. This is shown in FIG. 5, also illustrating the next position of the dosing device 20a.

After the third membrane 152 has been penetrated, whereby the dosing device 20b is positioned to provide transfer of the associated food ingredient FI, the second chamber 120 is again flushed with steam S, forming a sterile condensate inside the second chamber 120.

When transfer of the food ingredient FI is finished, the dosing device 20b may be removed from the first and second chambers 110, 120, thus returning to the position shown in FIG. 2.

Figure 6:
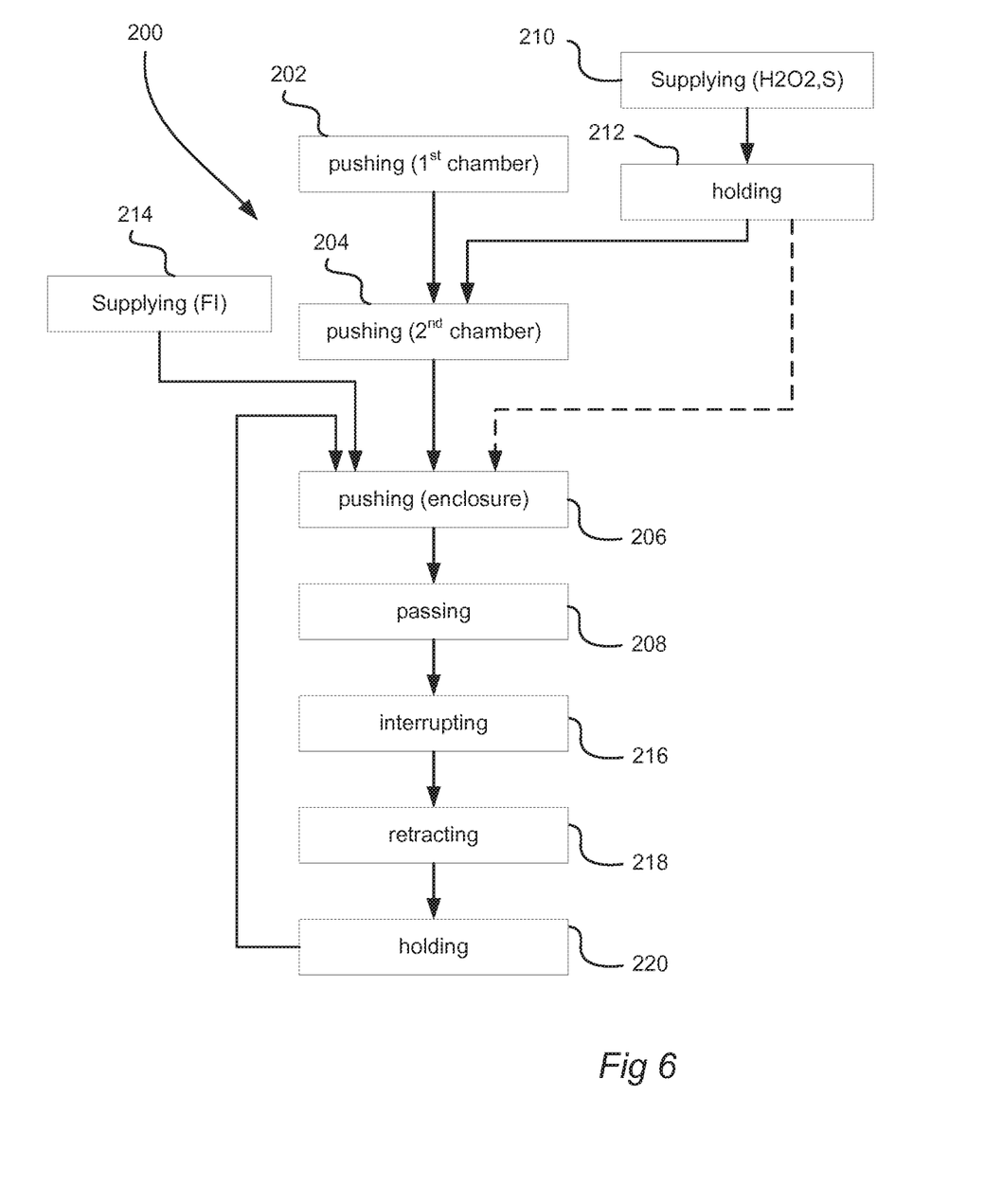
FIG. 6 is a schematic view of a method for transferring a food ingredient.

In FIG. 6 a more detailed view of a method 200 for transferring a food ingredient FI is shown, as performed for a food ingredient transfer device similar to the device 100 described above.

Generally, the method 200 comprises pushing 202 the dosing device 20b through the first chamber 110 that is provided with the inlet 112b and the outlet 114b for allowing the dosing device 20b to pass through the first chamber 110. Subsequently, the method 200 comprises pushing 204 the dosing device 20b through the second chamber 120 that is arranged adjacent to the first chamber 110 and provided with the outlet 124b for allowing the dosing device 20b to pass through the second chamber 120. The method 200 proceeds in pushing 206 the dosing device 20b into the enclosure 40 that is arranged adjacent to the second chamber 120 and contains a food product FP that shall receive the food ingredient FI, and passing 208 the food ingredient FI through the dosing device 20b, into the food product FP in the enclosure 40.

During this sequence, a number of additional method steps may be performed. For example, the method 200 may also comprise a step of supplying 210 a sterilizing agent, such as steam or hydrogen peroxide H2O2, to any of the first chamber 110 and the second chamber 120, and a step of holding 212 the dosing device 20b a predetermined time in the chamber 110, 120 to which the sterilizing agent was supplied in step 210, such that the dosing device 20b, or more specifically the part of the dosing device 20b that is located inside the chamber 110, 120, is sterilized before it is pushed 206 into the enclosure 40 that contains the food product FP.

As is shown in FIG. 6, steps 210 and 212 (i.e. supplying sterilizing agent and holding) may be performed to supply hydrogen peroxide to the first chamber 110 and maintaining the dosing device 20b stationary for a predetermined time period, or they may be performed to supply steam to the second chamber 120 and maintaining the dosing device stationary for a predetermined time period.

In the first case, indicated by a solid line in FIG. 6, the method 200 may additionally comprise the step 214 of supplying steam S to the second chamber 120.

After passing, in step 208, the food ingredient FI into the food product FP the method 200 may continue by interrupting 216 any passing of the food ingredient through the dosing device 20b, retracting 218 the dosing device 20b from the enclosure 40, until a distal end 22 of the dosing device 20b is located in the chamber 110, 120 to which the sterilizing agent was supplied 210, and holding 220 the dosing device 20b a predetermined time in the chamber 110, 120 to which the sterilizing agent was supplied 210, such that the dosing device is sterilized before it is again pushed 206 into the enclosure 40.

Other sterilization agents than hydrogen peroxide may be used. Also, another agent than steam may be used. It is also possible to use more than the two food dosing devices with corresponding openings and membranes in the food ingredient transfer device.

From the description above follows that, although various embodiments of the invention have been described and shown, the invention is not restricted thereto, but may also be embodied in other ways within the scope of the subject-matter defined in the following claims.

The invention claimed is:

1. A food ingredient transfer device, comprising:
a dosing device configured to receive a food ingredient, and
a first chamber that is provided with an inlet and an outlet for allowing the dosing device to pass through the first chamber,
a second chamber that is arranged adjacent to the first chamber for receiving the dosing device when it has passed through the first chamber, the second chamber being provided with an outlet for allowing the dosing device to pass through the second chamber and into an enclosure that contains a food product to which the food ingredient shall be transferred, wherein:
a first penetrable membrane is arranged to seal the inlet of the first chamber,
a second penetrable membrane is arranged to seal the outlet of the first chamber,
a third penetrable membrane is arranged to seal the outlet of the second chamber,
the first penetrable membrane, the second penetrable membrane, and the third penetrable membrane being aligned in a linear direction that extends from the first penetrable membrane to the third penetrable membrane,
the first chamber comprising an inlet port and an outlet port for receiving and respectively expelling a first fluid, and the second chamber comprising an inlet port and an outlet port for receiving and respectively expelling a second fluid.

2. The food ingredient transfer device according to claim 1, wherein the first chamber is provided with at least two inlets and a corresponding number of outlets, and wherein the second chamber is provided with a corresponding number of outlets for allowing at least two dosing devices, which are configured to receive the food ingredient, to pass through the first and second chambers and into the enclosure that contains the food product to which the food ingredient shall be transferred.

3. The food ingredient transfer device according to claim 1, wherein the first fluid is a sterilizing agent, the food ingredient transfer device further comprising a supply of the sterilization agent in fluid communication with the first chamber.

4. The food ingredient transfer device according to claim 1, wherein the second fluid is steam, the food ingredient transfer device further comprising a supply of the steam in fluid communication with the second chamber.

5. The food ingredient transfer device according to claim 3, comprising a controller configured to control
supply of the first fluid to the first chamber,
supply of the second fluid to the second chamber, and
passing of the dosing device through the first and second chambers.

6. The food ingredient transfer device according to claim 5, wherein the controller is configured to control any of a temperature, a pressure and a concentration of any of the first fluid and the second fluid.

7. A method of transferring Hall the food ingredient with a food ingredient transfer device according to claim 1, the method comprising:
pushing the dosing device through the first chamber that is provided with the inlet and the outlet for allowing the dosing device to pass through the first chamber,
pushing the dosing device through the second chamber that is arranged adjacent to the first chamber and provided with the outlet for allowing the dosing device to pass through the second chamber,
pushing the dosing device into Drill the enclosure that is arranged adjacent to the second chamber and contains the food product that shall receive the food ingredient, and
passing the food ingredient through the dosing device, into the food product in the enclosure.

8. The method of transferring a food ingredient according to claim 7, comprising
supplying a sterilizing agent to any of the first chamber and the second chamber,
holding the dosing device a predetermined time in the chamber to which the sterilizing agent was supplied, such that the dosing device is sterilized before it is pushed into the enclosure that contains the food product.

9. The method of transferring a food ingredient according to claim 8, wherein the sterilizing agent is supplied to the first chamber, the method comprising
supplying steam to the second chamber.

10. The method of transferring a food ingredient according to claim 8, comprising
interrupting any passing of the food ingredient through the dosing device,
retracting the dosing device from the enclosure, until a distal end of the dosing device is located in the chamber to which the sterilizing agent was supplied,
holding the dosing device a predetermined time in the chamber to which the sterilizing agent was supplied, such that the dosing device is sterilized before it is again pushed into the enclosure.

11. The food ingredient transfer device according to claim 1, wherein the dosing device is a dosing needle.

12. The food ingredient transfer device according to claim 3, wherein the sterilizing agent is hydrogen peroxide.

13. The method according to claim 7, wherein the dosing device is a dosing needle.

* * * * *